United States Patent
Zaugg (10) Patent No.: US 7,292,342 B2
(45) Date of Patent: Nov. 6, 2007

(54) ENTANGLED PHOTON FOURIER TRANSFORM SPECTROSCOPY

(75) Inventor: Thomas Zaugg, Ypsilanti, MI (US)

(73) Assignee: General Dynamics Advanced Information Systems Inc., Arlington, VA (US)

( * ) Notice: Subject to any disclaimer, the term of this patent is extended or adjusted under 35 U.S.C. 154(b) by 447 days.

(21) Appl. No.: 10/900,403

(22) Filed: Jul. 28, 2004

(65) Prior Publication Data

US 2005/0206904 A1    Sep. 22, 2005

Related U.S. Application Data (60) Provisional application No. 60/540,011, filed on Jan. 30, 2004.

(51) Int. Cl.
*G01B 9/02*    (2006.01)

(52) U.S. Cl. .................................... 356/451

(58) Field of Classification Search ............ 356/328, 356/334, 450, 451
See application file for complete search history.

(56) References Cited

U.S. PATENT DOCUMENTS

| | | | |
|---|---|---|---|
| 4,225,938 A | 9/1980 | Turpin | |
| 4,286,328 A | 8/1981 | Bocker | |
| 4,468,093 A | 8/1984 | Brown | |
| 4,633,427 A | 12/1986 | Bocker | |
| 5,339,182 A | 8/1994 | Kimble et al. | |
| 5,420,905 A | 5/1995 | Bertozzi | |
| 5,796,477 A | 8/1998 | Teich et al. | |
| 5,917,322 A | 6/1999 | Gershenfeld et al. | |
| 6,057,541 A | 5/2000 | Steenblik | |

(Continued)

FOREIGN PATENT DOCUMENTS

EP    1091240    4/2001

(Continued)

OTHER PUBLICATIONS

Strekalov et al., Two-photon processes in faint biphoton fields, pp. 1-18, downloaded Mar. 9, 2005, http://arxiv.org.

(Continued)

*Primary Examiner*—Hwa (Andrew) Lee
*Assistant Examiner*—Marissa J. Detschel
(74) *Attorney, Agent, or Firm*—Hunton & Williams LLP; Jeffrey Scott Leaning (57) ABSTRACT

Novel spectroscopy techniques using entangled photons are disclosed. In one technique, entangled photons are directed to a sample of interest, while the photons with which they are entangled are resolved according to frequency. The photons transmitted by or reflected from the sample and the frequency-resolved photons are detected. Such detection may be by way of an electronic coincidence counter or a biphoton sensitive material, which absorbs entangled photons while allowing other photon pairs to pass. Detection information is used to derive spectroscopic properties of the sample. In another technique, a Fourier transform spectroscopy technique using entangled photons is disclosed. Entangled photons are directed to a sample, while the photons with which they are entangled are directed to a Michelson interferometer. The photons transmitted by or reflected from the sample and the photons leaving the Michelson interferometer are detected. Such detection may be by way of an electronic coincidence counter or a biphoton sensitive material. Detection information is used to derive spectroscopic properties of the sample.

61 Claims, 6 Drawing Sheets

U.S. PATENT DOCUMENTS

| | | | |
|---|---|---|---|
| 6,252,665 B1 | 6/2001 | Williams et al. | |
| 6,289,104 B1 | 9/2001 | Patterson et al. | |
| 6,314,189 B1 | 11/2001 | Motoyoshi et al. | |
| 6,430,345 B1 | 8/2002 | Dultz et al. | |
| 6,444,999 B1 | 9/2002 | Tomita | |
| 6,473,719 B1 | 10/2002 | Steenblik | |
| 6,480,283 B1 | 11/2002 | Williams et al. | |
| 6,522,749 B2 | 2/2003 | Wang | |
| 6,424,665 B1 | 7/2003 | Kwiat et al. | |
| 6,646,727 B2 | 11/2003 | Saleh et al. | |
| 6,678,054 B1 | 1/2004 | Dress et al. | |
| 6,822,739 B2* | 11/2004 | Sergienko et al. | 356/369 |
| 7,046,366 B2* | 5/2006 | Ozeki et al. | 356/477 |
| 2002/0018290 A1 | 2/2002 | Birk et al. | |
| 2002/0020819 A1 | 2/2002 | Wolleschensky et al. | |
| 2002/0036775 A1 | 3/2002 | Wolleschensky et al. | |
| 2002/0093632 A1 | 7/2002 | Teich et al. | |
| 2002/0109840 A1 | 8/2002 | Wolleschensky et al. | |
| 2002/0140941 A1 | 10/2002 | Pedigo | |
| 2003/0002670 A1 | 1/2003 | Wang | |
| 2003/0086138 A1* | 5/2003 | Pittman et al. | 359/108 |
| 2004/0036877 A1 | 2/2004 | Sergienko et al. | |
| 2004/0208638 A1 | 10/2004 | Jansen | |
| 2005/0006593 A1* | 1/2005 | Kastella et al. | 250/458.1 |

FOREIGN PATENT DOCUMENTS

| | | |
|---|---|---|
| WO | WO 02/454468 A2 | 6/2002 |
| WO | WO 03/019282 A2 | 3/2003 |
| WO | WO 03/019283 A2 | 3/2003 |
| WO | WO 03/019284 A2 | 3/2003 |

OTHER PUBLICATIONS

Enzer et al., Entangled-photon six-state quantum cryptography, New Journal of Physics 4 (2002) 45.1-45.8.

Gatti et al., Multi-photon, multi-mode polarization entanglement in parametric down-conversion, pp. 1-22 (download date unknown), http://arxiv.org.

Bouwmeester et al., Experimental quantum teleportation, Nature, vol. 390, Dec. 11, 1997, pp. 575-579.

Sciarrino et al., Delayed-choice entanglement swapping with vacuum-one-photon quantum states, Physical Review A, 66, 024309 (2002).

Sergienko et al., Quantum cryptography with femtosecond parametric down conversion, Quantum Imaging Laboratory, pp. 1-8.

Altepeter et al., Ancilla-assisted quantum process tomography, Physical Review Letters, vol. 90, No. 19, May 16, 2003, 193601- to 193601-4.

Oneil, Quantum information studies, Department of Experimental Physics, {http://www.may.ie/academic/physics/quantum.shtml}, printed Feb. 25, 2004, 2 pages.

Giacomini et al., Active teleportation of a quantum bit, Physical Review A, 66, 030302(R) (2000).

Jost et al., Spatial correlations of spontaneously down-converted photon pairs detected with a single-photon-sensitive CCD camera, Optics Express 81, Jul. 20, 1998, vol. 3, No. 2.

Caetano et al., Quantum image control through polarization entanglement in parametric down-conversion, Physical Review A 68, 023805 (2003).

Barbosa, Twin photons entangled in polarization and angular momentum, Eur. Phys. J. D22, 433-440 (2003).

Ribeiro, Image and coherence transfer in the stimulated down-conversion process, Physical Review A, vol. 60, No. 6, Dec. 1999, 5074-5078.

Monken et al., Transfer of angular spectrum and image formation in spontaneous parametric down-conversion, Physical Review A, vol. 57, No. 4, Apr. 1998, 3123-3126.

Ribeiro et al., Observation of image transfer and phase conjugation in stimulated down-conversion, Physical Review Letters, vol. 87, No. 13, Sep. 24, 2001, 133602-1 to 133602-4.

Fonseca et al., Quantum interference by a nonlocal double slit, Physical Review A, vol. 60, No. 2, Aug. 1999, 1530-1533.

Atature et al., Entanglement in cascaded-crsytal parametric down-conversion, Physical Review Letters, vol. 86, No. 18, Apr. 30, 2001, 4013-4016.

White et al., Nonmaximally entangled states: production, characterization, and utilization, Physical Review Letters, vol. 83, No. 16, Oct. 18, 1999, 3103-3107.

Kwiat et al., Ultrabright source of polarization-entangled photons, Physical Review A, vol. 60, No. 2, Aug. 1999, 773-776.

Kwiat et al., Experimental entanglement distillation and "hidden" non-locality, Letter to Nature, 1014-1017, 2001.

Grover, Quantum computers can search arbitrarily large databases by a single query, Physical Review Letters vol. 79, No. 23, Dec. 8, 1997, 4709-4712.

Berthiaume et al., The quantum challenge to structural complexity theory, 132-137.

Ekert et al., Quantum computation and Shor's factoring algorithm, Reviews of Modern Physics, vol. 68, No. 3, Jul. 1996, 733-753.

Zhang et al., Experimental and theoretical aspects of quantum teleportation, Center for Engineering Science Advanced Research, 9 pages.

Abouraddy et al., Degree of entanglement for two qubits, Physical Review A, vol. 64, 050101-1 to 050101-4.

Semat et al., Introduction to Atomic and Nuclear Physics, Fifth Edition, Chp. 7, Elements of quantum mechanics, 186-215.

Ekert, Quantum cryptography based on Bell's theorem, Physical Review Letters, vol. 67, No. 6, Aug. 5, 1991, 661-663.

Schenker, A quantum leap in codes for secure transmissions, International Herald Tribune, printed Apr. 12, 2004, {http://www.iht.com/articles/126822.html}, 3 pages.

Johnson, Magiq employs quantum technology for secure encryption, Advanced Technology, printed Apr. 12, 2004 {http://www.eetimes.com/at/news/OEG20021105S0019}, 3 pages.

McCulagh, Start-up makes quantum leap into cryptography, C/NET News.com, printed Apr. 12, 2004, {http://news.com.com/2100-1029-5103373.html}, 3 pages.

Scully et al., Two-photon scheme for detecting the Bell basis using atomic coherence, Physical Review Letters, vol. 83, No. 21, Nov. 22, 1999, 4433-4436.

Braunstein et al., Dense coding for continuous variables, Physical Review A, vol. 61, 042302-1 to 04302-4.

Santos et al., Measurement of the degree of polarization entanglement through position interference, Physical Review A, vol. 64, 023804-1 to 023804-6.

Saleh et al., Entangled-photon virtual-state spectroscopy, Physical Review Letters, vol. 80, No. 16, Apr. 20, 1998, 3483-3486.

Oberparleiter et al., Optics Communications, 183 (2000) 133-137.

Georgiades et al., Nonclassical excitation for atoms in a squeezed vacuum, Physical Review Letters, vol. 75, No. 19, Nov. 6, 1995, 3426-3429.

Joobeur et al., Spatiotemporal coherence properties of entangled light beams generated by parametric down-conversion, Physical Review A, vol. 50, No. 4, Oct. 1994, 3349-3361.

Nasr et al., Biphoton focusing for two-photon excitation, Physical Review A, vol. 65, 023816-1 to 023816-6.

Abouraddy et al., Role of entanglement in two-photon imaging, Physical Review Letters, vol. 87, No. 12, Sep. 17, 2001, 123602-1 to 123602-4.

Boeuf et al., Calculating characteristics of non-collinear phase-matching in uniaxial biaxial crystals, Optical Technology Division, pp. 1-24.

Abouraddy et al., Double-slit interference of biphotons generated in spontaneous parametric downconversion from a thick crystal, Journal of Optics B: Quantum and Semiclassical Optics 3, 2001, S50-S54.

Kwiat et al., Experimental verification of decoherence-free subspaces, Science, vol. 290, Oct. 20, 2000, 498-500.

Naik et al., Entangled state quantum cryptography: eavesdropping on the Eckert protocol, Physical Review Letters, vol. 84, No. 20, May 15, 2000, 4733-4736.

Yabushita et al., Spectroscopy by frequency entangled photon pairs, pp. 1-11(download date unknown), http://arxiv.org.

Perina et al., Multiphoton absorption cross section and virtual-state spectroscopy for the entangled $n$-photon state, Physical Review A, vol. 57, No. 5, May 1998, pp. 3972-3986.

Fei et al., Entangled-induced two-photon transparency, Physical Review Letters, vol. 78, No. 9, Mar. 3, 1997, pp. 1679-1682.

Yabushita et al., Spectroscopy by frequency entangled photon pairs, Physical Review A 69. 013806-1-013806-4 (2004).

Kurtsiefer et al., High-efficiency entangled photon pair collection in type-II parametric fluorescence, Physical Review A, vol. 64, 023802-1 to 023802-4.

Almeida et al., Transmission of quantum images through long distances, pp. 1-4, (download date unknown), http://arxiv.org.

Caetano et al., Quantum Physics, Abstract, Image formation by manipulation of the entangled angular spectrum, pp. 1-5, (download date unknown), http://arxiv.org.

Zavatta, Premio Italgas/Italgas Prize Energy and Environment 16th Edition, Summary of the Thesis "Debut in the World of Research".

Rubin et al., Theory of two-photon entanglement in type-II optical parametric down-conversion, Physical Review A, vol. 50, No. 6, Dec. 1994, pp. 5122-5133.

Rarity et al., Experimental demonstration of single photon rangefinding using parametric downconversion, Applied Optics, vol. 29, No. 19, Jul. 1, 1990, pp. 2939-2943.

Waks et al., Security of quantum key distribution with entangled photons against individual attacks, Physical Review A, vol. 65, 052310-1 to 052310-16, 2002.

Caetano et al., Image-polarization entanglement in parametric down-conversion, 4 pages.

Caetano et al., Quantum distillation of position entanglement with the polarization degrees of freedom, ScienceDirect, Optics Communications, Mar. 3, 2004, (www.sciencedirect.com/science).

* cited by examiner

ENTANGLED PHOTON FOURIER TRANSFORM SPECTROSCOPY

RELATED APPLICATIONS

The present application claims priority to U.S. Provisional Application Ser. No. 60/540,011 entitled "Entangled-photon Fourier Transform Spectrometer" to Zaugg, filed Jan. 30, 2004, and is related to U.S. Utility Application Ser. No. 10/850,394 entitled "System and Method of Detecting Entangled Photons" to Kastella et al., filed May 21, 2004, the disclosures of which are expressly incorporated by reference herein in their entireties.

FIELD OF THE INVENTION

The present invention relates to spectroscopy. In particular, the present invention relates to absorption spectroscopy using entangled photons.

BACKGROUND OF THE INVENTION

Techniques for performing spectroscopy are known. In many of these techniques, light from a broadband source, (e.g., a tungsten filament lamp), impinges upon a sample and is then separated into spectral components via a prism or grating. The prism or grating is rotated to bring each spectral component in turn into a detector where a measurement is performed. In other known spectroscopy techniques, tunable narrowband light sources (e.g. lasers) are directed at a sample, and the transmitted light is detected.

While traditional absorption methods in the near and mid-infrared regions may be performed, such techniques suffer from poor sensitivity due to low resolution and low sensitivities of available detectors. Far-infrared (far-IR) and terahertz (THz) spectral regions are not easily accessible using current technology, yet these bands are rich in spectroscopic information. Another disadvantage of existing techniques is the requirement for cumbersome and frequent calibration. Further, in conventional spectroscopy, noise from background radiation degrades both resolution and signal-to-noise ratio (SNR).

Photons are quanta of electromagnetic energy. Multiple photons may be random or entangled. Random photons are not entangled together and exist as independent entities. In contrast, entangled photons have a connection between their respective properties.

Two photons entangled together are referred to as an entangled-photon pair (also, "biphotons"). Traditionally, photons comprising an entangled-photon pair are called "signal" and "idler" photons. Measuring properties of one photon of an entangled-photon pair determines properties of the other photon, even if the two entangled photons are separated by a distance. As understood by those of ordinary skill in the art and by way of non-limiting example, the quantum mechanical state of an entangled-photon pair cannot be factored into a product of two individual quantum states.

Photon properties that may be entangled include time, frequency, and angular momentum. Photons that are entangled in time are generated nearly simultaneously. For given optical path lengths traveled by constituent photons in a temporally-entangled-photon pair, detecting one of the photons places limits on the times at which the other photon may be detected. Photons that are entangled together in frequency have their frequencies related, in that measuring the frequency of one such photon determines the frequency of the photon with which it is entangled to within the bandwidth of the originating pump photon (for biphotons produced via a spontaneous parametric downconversion process).

SUMMARY OF THE INVENTION

Conventional spectrometers have several drawbacks. First, known spectrometers that employ dispersive elements are quite sensitive to background radiation, which limits their performance and sensitivity. Second, existing spectrometers are limited in the range of frequency information that they can detect. In particular, far-IR and THz frequency bands, which are rich in spectroscopic information, are difficult to access with conventional absorption spectroscopy. Third, calibration of conventional spectrometers requires calibrating the power source at the time of measurement, and fluctuations in power often result in decreased sensitivity. Fourth, conventional broadband spectrometers require high fluxes that can damage samples. Fifth, conventional spectrometers afford less versatility in measuring absorption over long distances, such as in analyzing atmospheric species, or in medical applications. And sixth, conventional spectrometers are sensitive to re-radiated energy, which can be a source of additional noise in the measurement.

Entangled-photon spectrometer embodiments according to the present invention substantially overcome the aforementioned limitations. Biphotons can be generated such that the signal and idler beams have different center frequencies, which presents the possibility of performing spectroscopy in the far-IR and THz frequency bands that are otherwise difficult to access. Moreover, such novel embodiments disclosed herein use off-the-shelf dispersive elements designed for visible or near-IR bands. Further, embodiments of the present invention are resistant to background radiation, which makes possible the use of entangled-photon spectroscopy over very long distances, e.g., for identification of atmospheric contaminants. Existing long-distance sensors are typically limited to a few narrow frequency bands using lasers that may pose environmental hazards. In contrast, the light levels required for embodiments of the present invention are completely benign and neither degrade the sample of interest nor pose an environmental hazard. Entangled-photon spectrometer embodiments according to the present invention are insensitive to re-radiated energy. For electronic coincidence counter embodiments of the present invention, the sensitivity of the spectrometer can be increased as needed by increasing an easily-manipulated parameter known as integration time. In addition, unlike conventional spectrometers, the only calibration necessary for embodiments of the present invention is a determination of the quantum efficiency of the detector, which can be calibrated by simply removing the sample. That is, an embodiment of the present invention may be calibrated by operating it without a sample present and thereby determining the quantum efficiency of at least one of the detectors. The quantum efficiency of the detector does not change under normal conditions. Because spectrographic information is measured according to embodiments of the present invention in one of two entangled-photon beams, the detector can be positioned to measure reflected or scattered light at any angle by simply moving the detector. Such flexibility in a conventional spectrometer would result in significant increases in the complexity of the device and difficulty in calibration.

According to an embodiment of the invention, a method of performing entangled-photon absorption spectroscopy is provided. Pump photons are converted into pairs of signal and idler photons. The signal photons are directed at a sample, and those that are not absorbed by (or those that are reflected from) the sample are detected. The idler photons are resolved spectrally by a frequency resolving apparatus such as a prism or grating and are then detected using a plurality of bins corresponding to a plurality of frequencies. Alternately, a single idler photon detector could be used to collect photons for a narrow range of frequencies and the angle of the prism or grating may be changed, with different frequency data collected for each angle. A device for extracting a narrow range of frequencies with a controllable center frequency from a broader source is called a monochromator. A commercial monochromator (which may include multiple prisms or gratings) may be used in the place of a single dispersive element. That is, dispersive elements or monochromators, which incorporate dispersive elements, may be used. Because the biphotons are entangled in frequency, a measurement of the frequency of the idler photon determines the frequency of the signal photon of the entangled photon pair. Because the biphotons are also entangled in time, the difference in time between the two detection events will be less than the entanglement time (accounting for any path difference). The detection of a signal and idler photon within a short time interval called the coincidence window results in a coincidence count. Accounting for accidental coincidences, the coincident count rate for each idler frequency bin is proportional to the transmittance of the sample at the corresponding signal frequency. The ratio of coincidence counts to idler counts for each idler frequency bin corresponds to the transmittance of the sample at the corresponding signal frequency multiplied by the quantum efficiency of the signal detector.

According to another embodiment of the invention, an entangled-photon Fourier transform spectrometer is provided. An entangled-photon Fourier transform spectrometer is constructed using a Michelson interferometer. The coincidence count rate for each interferometer setting is recorded. The set of collected measurements is converted into an absorption (or reflection) spectrum via an inverse cosine transform.

Various optional and preferable features of the above embodiments include using a single detector in the idler path and rotating the dispersive element so as to select the frequency for which a measurement is to be made. Any combination of multiple detectors and rotation (or other means) for selecting measurement frequencies is also contemplated.

According to another embodiment of the invention, an entangled-photon spectrometer capable of measuring reflected light is provided. In a reflection geometry, the sample may be at stand-off distances, yielding a high resolution reflection spectrum of the illuminated area, yet using incoherent low-level illumination. The sample may be placed in the idler photon path, yielding resolution that is not limited by the pump bandwidth, but still benefiting from the signal-to-noise ratio advantage possible with coincidence counting. That is, such embodiments ignore background photons counted by the idler system since they will not (except at random) be coincident with detected signal photons.

According to another embodiment of the invention, a method of determining spectroscopic information of a portion of matter is provided. The method includes producing a first photon beam and a second photon beam, each photon in at least a portion of the first photon beam being entangled with at least one photon in the second photon beam. Photons from the first photon beam interact with the portion of matter to produce first photons. The second beam is processed to produce second photons. At least one coincidence is detected, each coincidence occurring between a first photon and a second photon, to derive a coincidence parameter. The coincidence parameter is used to derive spectroscopic information relating to the portion of matter.

Various optional and preferable features of the above embodiment include the following. The first photons may include photons transmitted by the portion of matter, photons reflected by the portion of matter, or photons scattered by the portion of matter. The processing may include processing with an interferometer. The interferometer may be a Michelson interferometer or a Mach-Zender interferometer. The processing may include selecting a frequency. The processing may include separating by frequency. The detecting may include using an electronic coincidence counter. The detecting may include using an entangled photon sensitive material. The coincidence parameter may include a number of coincidences in a time interval. The coincidence parameter may include a ratio of coincidence detection counts. The first photon beam may include far infrared or terahertz photons. The portion of matter may be remote from a location of the detecting. The method may include calibrating, where the calibrating includes determining a quantum efficiency of a detector, the detector being configured to detect at least a portion of the first photons.

According to another embodiment of the invention, a system for determining spectroscopic information of a portion of matter is provided. The system includes means for producing a first photon beam and a second photon beam, each photon in at least a portion of the first photon beam being entangled with at least one photon in the second photon beam. The system also includes means for processing the second beam to produce processed photons. The system further includes means for detecting at least one coincidence, each coincidence occurring between a photon that has interacted with the portion of matter and a processed photon, to derive a coincidence parameter. A computer is configured to use the coincidence parameter to derive spectroscopic information relating to the portion of matter.

Various optional and preferable features of the above embodiment include the following. The means for detecting may include a means for detecting at least one coincidence, each coincidence occurring between a processed photon and a photon transmitted by the portion of matter, a photon reflected by the portion of matter, or a photon scattered by the portion of matter. The means for processing may include an interferometer. The interferometer may be a Michelson interferometer or a Mach-Zender interferometer. The means for processing may include a monochromator. The means for processing may include a dispersive element. The means for detecting may include an electronic coincidence counter. The means for detecting may include an entangled photon sensitive material. The coincidence parameter may include a number of coincidences in a time interval. The coincidence parameter may include a ratio of coincidence detection counts. The first photon beam may include far infrared or terahertz photons. The portion of matter may be remote from the means for detecting. The system may be configured to be calibrated by determining a quantum efficiency of a detector, the detector being configured to detect at least a portion of the photons that have interacted with the portion of matter.

According to another embodiment of the invention, a system for determining spectroscopic information of a portion of matter is provided. The system includes a source of entangled photons and optics configured to receive a first portion of photons, where the first portion of photons have interacted with the portion of matter. The first portion of photons include a portion of the entangled photons. The system also includes a dispersive element configured to receive a second portion of photons and output a third portion of photons, each photon in the second portion of photons being entangled with at least one photon in the first portion of photons. The system further includes a coincidence counter configured to detect at least one coincidence, each coincidence occurring between a photon in the first portion of photons and a photon in the third portion of photons, to derive a coincidence parameter. A computer is configured to use the coincidence parameter to derive spectroscopic information relating to the portion of matter.

Various optional and preferable features of the above embodiment include the following. The first portion of photons may include photons transmitted by the portion of matter, photons reflected by the portion of matter, or photons scattered by the portion of matter. The system may include a monochromator including the dispersive element. The coincidence counter may include an electronic coincidence counter. The coincidence counter may include an entangled photon sensitive material. The coincidence parameter may include a number of coincidences in a time interval. The coincidence parameter may include a ratio of coincidence detection counts. The first portion of photons may include far infrared photons or terahertz photons. The portion of matter may be remote from the means for detecting. The system may be configured to be calibrated by determining a quantum efficiency of a detector, the detector being configured to detect at least a portion of the first portion of photons.

According to another embodiment of the invention, a system for determining spectroscopic information of a portion of matter is provided. The system includes a source of entangled photons and optics configured to receive a first portion of photons, the first portion of photons having interacted with the portion of matter. The first portion of photons include a portion of the entangled photons. The system also includes an interferometer configured to receive a second portion of photons and output a third portion of photons, each photon in the second portion of photons being entangled with at least one photon in the first portion of photons. The system further includes a coincidence counter configured to detect at least one coincidence, each coincidence occurring between a photon in the first portion of photons and a photon in the third portion of photons, to derive a coincidence parameter. A computer is configured to use the coincidence parameter to derive spectroscopic information relating to the portion of matter.

Various optional and preferable features of the above embodiment include the following. The first portion of photons may include photons transmitted by the portion of matter, photons reflected by the portion of matter, or photons scattered by the portion of matter. The interferometer may be a Michelson interferometer or a Mach-Zender interferometer. The coincidence counter may include an electronic coincidence counter. The coincidence counter may include an entangled photon sensitive material. The coincidence parameter may include a number of coincidences in a time interval. The coincidence parameter may include a ratio of coincidence detection counts. The first portion of photons may include far infrared photons or terahertz photons. The portion of matter may be remote from the means for detecting. The system may be configured to be calibrated by determining a quantum efficiency of a detector, the detector being configured to detect at least a portion of the first portion of photons.

According to another embodiment of the invention, a method of determining spectroscopic information of a portion of matter is provided. The method includes producing a first photon beam and a second photon beam, each photon in at least a portion of the first photon beam being entangled with at least one photon in the second photon beam. The method also includes directing photons from the first photon beam to interact with the portion of matter to produce first photons. The method further includes causing a first portion of photons from the second photon beam to interfere with a second portion of photons from the second photon beam to produce second photons. At least one coincidence is detected, each coincidence occurring between a first photon and a second photon, to derive a coincidence parameter. The coincidence parameter is used to derive spectroscopic information relating to the portion of matter.

Various optional and preferable features of the above embodiment include the following. The first photons may include photons transmitted by the portion of matter, photons reflected by the portion of matter, or photons scattered by the portion of matter. The detecting may include using an electronic coincidence counter. The detecting may include using an entangled photon sensitive material. The coincidence parameter may include a number of coincidences in a time interval. The coincidence parameter may include a ratio of coincidence detection counts. The first photon beam may include includes far infrared photons or terahertz photons. The portion of matter may be remote from a location of the detecting. The method may include calibrating, where the calibrating includes determining a quantum efficiency of a detector, the detector being configured to detect at least a portion of the first photons. The causing may include using a Michelson interferometer or a Mach-Zender interferometer.

Other exemplary embodiments and advantages of the present invention may be ascertained by reviewing the present disclosure and the accompanying drawings.

BRIEF DESCRIPTION OF THE DRAWINGS

The present invention is further described in the detailed description which follows, in reference to the noted plurality of drawings by way of non-limiting examples of certain embodiments of the present invention, in which like numerals represent like elements throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, the description taken with the drawings provides a fundamental understanding of the present invention, making apparent to those skilled in the art how the several forms of the present invention may be embodied in practice.

Figure 1:
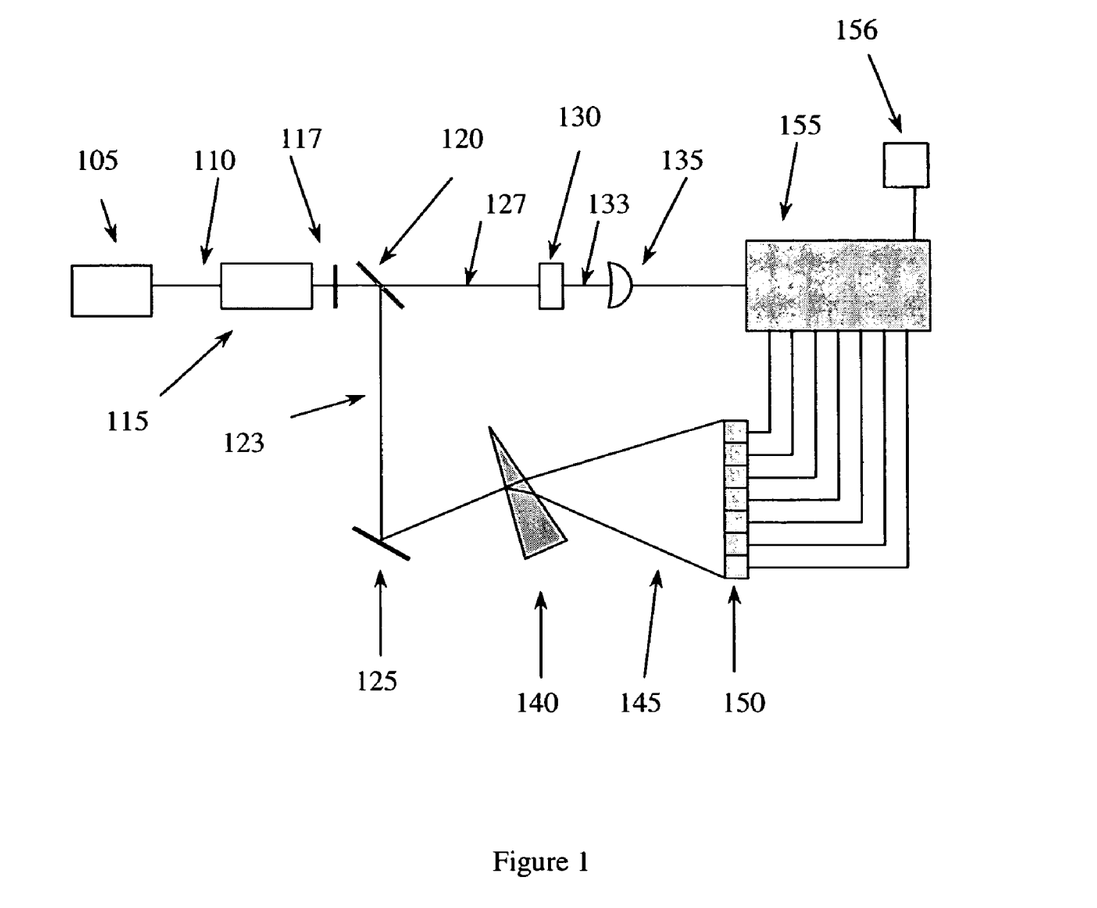
FIG. 1 is a schematic diagram of an entangled-photon spectrometer embodiment.

FIG. 1 is a schematic diagram of an entangled-photon absorption spectrometer embodiment. Pump beam 110 from laser 105 is directed to a nonlinear crystal 115 with a high second-order susceptibility, such as BBO ($\beta$-BaB$_2$O$_4$), to produce entangled-photon pairs via parametric downconversion. Filter 117 blocks remaining pump beam photons that may have passed through nonlinear crystal 115. The entangled-photon pairs are then separated into signal photons 127 and idler photons 123 by polarizing beam splitter 120. Next, signal photons 127 are directed at sample 130. Signal photons 133 that are not absorbed are detected by photon counting detector 135. The path length of the signal photon beam 127 can be varied as desired in different optical geometries. Idler photons 123 are sorted by frequency by dispersive element 140 (e.g., a prism or a grating). The idler photon frequency components 145 are detected by detector array 150. Detector array 150 includes a plurality of bins, each corresponding to a different frequency, and each capable of detecting a single photon. The signal photon detection events at detector 135 and idler photon detection events at detector array 150 are analyzed by coincidence counter 155. An idler photon detection event acts as a trigger, which begins timing a coincidence window. If a signal photon detection event occurs at detector 135 within the coincidence window, coincidence counter 155 registers a coincidence event. Computer 156 processes coincidence information in accordance with equations discussed below. To account for different optical path lengths between signal photons and idler photons, an electronic delay may be inserted between the idler photon detection event and the beginning of the coincidence window (assuming by way of non-limiting example that the signal photon path is the longer of the two optical paths).

The average biphoton coincidence count rate for each frequency bin can be written as, by way of non-limiting example:

$$\Phi_{cc\_bi}(\omega_j) = \int_{\omega_j - \frac{\Delta}{2}}^{\omega_j + \frac{\Delta}{2}} \Phi_{bi}(\omega) T(\omega) \eta_i(\omega_p - \omega) \eta_s(\omega) d\omega. \quad (1)$$

In equation (1), $\omega_j$ is the signal photon frequency corresponding to the center of the j-th idler frequency bin (note that $\omega_s = \omega_p - \omega_i$), $\Phi_{bi}(\omega)$ is the signal flux at frequency $\omega$ (or idler flux at frequency $\omega_p - \omega$), $T(\omega)$ is the sample transmittance at the frequency $\omega$, $\Delta$ is the bandwidth of each frequency bin, and $\eta_i$ and $\eta_s$ are the frequency-dependent quantum efficiencies of the idler and signal detectors respectively. In equation (1), the coincidence window is assumed to be longer than the entanglement time and the coincidence delay is set to account for any optical path length difference for purposes of illustration and by way of non-limiting example. Assuming for the purpose of illustration that the biphoton flux, the sample transmittance, and the detector quantum efficiencies change little over a frequency bin, the biphoton coincidence count for the j-th bin may be written as, by way of non-limiting example:

$$\Phi_{cc\_bi}(\omega_j) \approx \Delta \Phi_{bi}(\omega_j) T(\omega_j) \eta_i(\omega_p - \omega_j) \eta_s(\omega_j). \quad (2)$$

Under these illustrative assumptions, the idler photon count rate for the j-th frequency bin may be written as, by way of non-limiting example:

$$\Phi_i(\omega_j) \approx \Delta \Phi_{bi}(\omega_j) \eta_i(\omega_p - \omega_j). \quad (3)$$

The ratio of the coincidence count rate corresponding to the j-th bin to the idler photon count rate at the j-th bin may be written as, by way of non-limiting example:

$$\frac{\Phi_{cc\_bi}(\omega_j)}{\Phi_i(\omega_j)} \approx T(\omega_j) \eta_s(\omega_j). \quad (4)$$

The ratio described above in reference to equation (4) is proportional to the sample transmittance. Calibration may be accomplished by determining the quantum efficiency of the signal photon detector 135, which can easily be done by removing the sample or placing the detector right after the beam splitter. According to equation (4), the quantum efficiency of the idler photon detectors of detector array 150 need not be calibrated, and uniformity among these detectors is relatively unimportant.

Accidental coincidence counts contribute to a background coincidence count rate. An accidental coincidence count occurs when an unrelated signal photon or an ambient background photon is detected within the coincidence window corresponding to an idler photon detection. The accidental coincidence count rate for the j-th frequency bin may be represented as, by way of non-limiting example:

$$\Phi_{cc\_bg}(\omega_j) = \Phi_i(\omega_j) T_c \int_\Omega [\Phi_{bi}(\omega) T(\omega) + \Phi_{bg}(\omega)] \eta_s(\omega) d\omega. \quad (5)$$

In equation (5), $T_c$ is the duration of the coincidence window, $\Phi_{bg}$ is the ambient background flux, and $\Omega$ is the range over which the signal photon detector 135 is sensitive. The term inside the integral is the signal (plus ambient) photon count rate at signal photon detector 135. Dividing equation (5) by the idler photon count rate yields, by way of non-limiting example:

$$\frac{\Phi_{cc\_bg}(\omega_j)}{\Phi_i(\omega_j)} = T_c \Phi_s. \quad (6)$$

Accordingly, the total coincidence count rate for the j-th frequency bin is the sum of the biphoton and accidental (background) count rates. Because the accidental count rate is proportional to the rate of counts at the signal photon detector 135, it can easily be removed from the total. The noise on the count rate is the shot noise associated with the total coincidence count rate, so the signal-to-noise ratio can be computed as, by way of non-limiting example:

$$SNR(\omega_j) = \frac{\Phi_{cc\_bi}(\omega_j)}{\sqrt{2B(\Phi_{cc\_bi}(\omega_j) + \Phi_{cc\_bg}(\omega_j))}} \quad (7)$$

$$= \frac{T(\omega_j) \eta_s(\omega_j) \sqrt{\Phi_i(\omega_j)}}{\sqrt{2B(T(\omega_j) \eta_s(\omega_j) + T_c \Phi_s)}}.$$

In equation (7), B is the bandwidth of the detector (inverse of the integration time). Preferably, $T_c\Phi_s \ll 1$ in order to avoid saturation of the signal photon detector 135. Sensitivity corresponds to the minimum change in transmittance that can be detected with a signal-to-noise ratio of unity. Under signal-limited conditions, the minimum change in transmittance may be represented as, by way of non-limiting example:

$$\Delta T_{min} = \frac{2}{\eta_s \Phi_i(\omega_j)\tau}. \quad (8)$$

In equation (8), $\tau$ is the integration time (1/B). Under background-limited conditions, the minimum change in transmittance may be represented as, by way of non-limiting example:

$$\Delta T_{min} = \frac{1}{\eta_s}\sqrt{\frac{2T_c\Phi_s}{\Phi_i(\omega_j)\tau}}. \quad (9)$$

The sensitivity of the system at each frequency for either $\omega_i$ or $\omega_s$ can be determined from the measured count rates if the quantum efficiency of the signal detector is known.

An advantageous feature of the embodiment of FIG. 1 is that the sample spectrum (e.g., absorption or reflection) can be measured over a frequency range different from the range of frequencies for which the frequency resolving system (e.g., prism 140) has been designed. The optics used in the frequency resolving system of the idler photon path may even be opaque over some or all of the frequencies for which the sample spectrum is measured.

Note that the embodiment of FIG. 1 and equations (1)-(9) may be adapted to accommodate any, or a combination, of absorption, reflection, transmission, and scattering spectroscopy.

Figure 2:
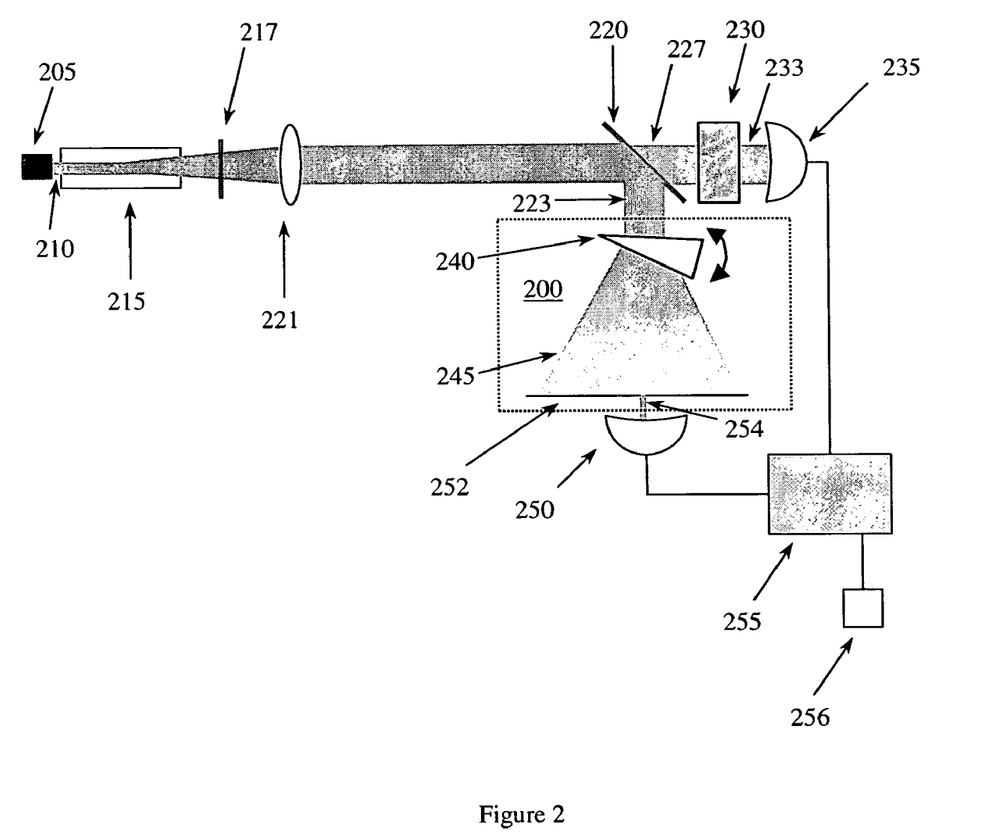
FIG. 2 is a schematic diagram of an entangled-photon spectrometer embodiment employing a monochromator.

FIG. 2 is a schematic diagram of an entangled-photon spectrometer embodiment employing a monochromator. As in the embodiment of FIG. 1, laser 205 produces pump beam 210, which is directed to nonlinear crystal 215. Filter 217 blocks remaining pump beam photons that may have passed through nonlinear crystal 215. Collimating lens 221 collimates the entangled photon pairs, which are then separated into signal photons 227 and idler photons 223 by polarizing beam splitter 220. Next, signal photons 227 are directed to sample 230. Signal photons 233 that are not absorbed are detected by signal photon detector 235. Idler photons 223 are directed to monochromator 200 (which could include a simple prism 240 or grating, followed by aperture 252), which selects idler photons 245 according to frequency. Idler photon detector 250 and signal photon detector 235 are operatively coupled to coincidence counter 255. As in the embodiment of FIG. 1, coincidence counter 255 feeds coincidence count information to computer 256, which processes the information as described above in reference to equations (1)-(9) in order to produce spectroscopic information regarding sample 230. The embodiment of FIG. 2 may be adapted to accommodate any, or a combination, of absorption, reflection, transmission, and scattering spectroscopy.

Figure 3:
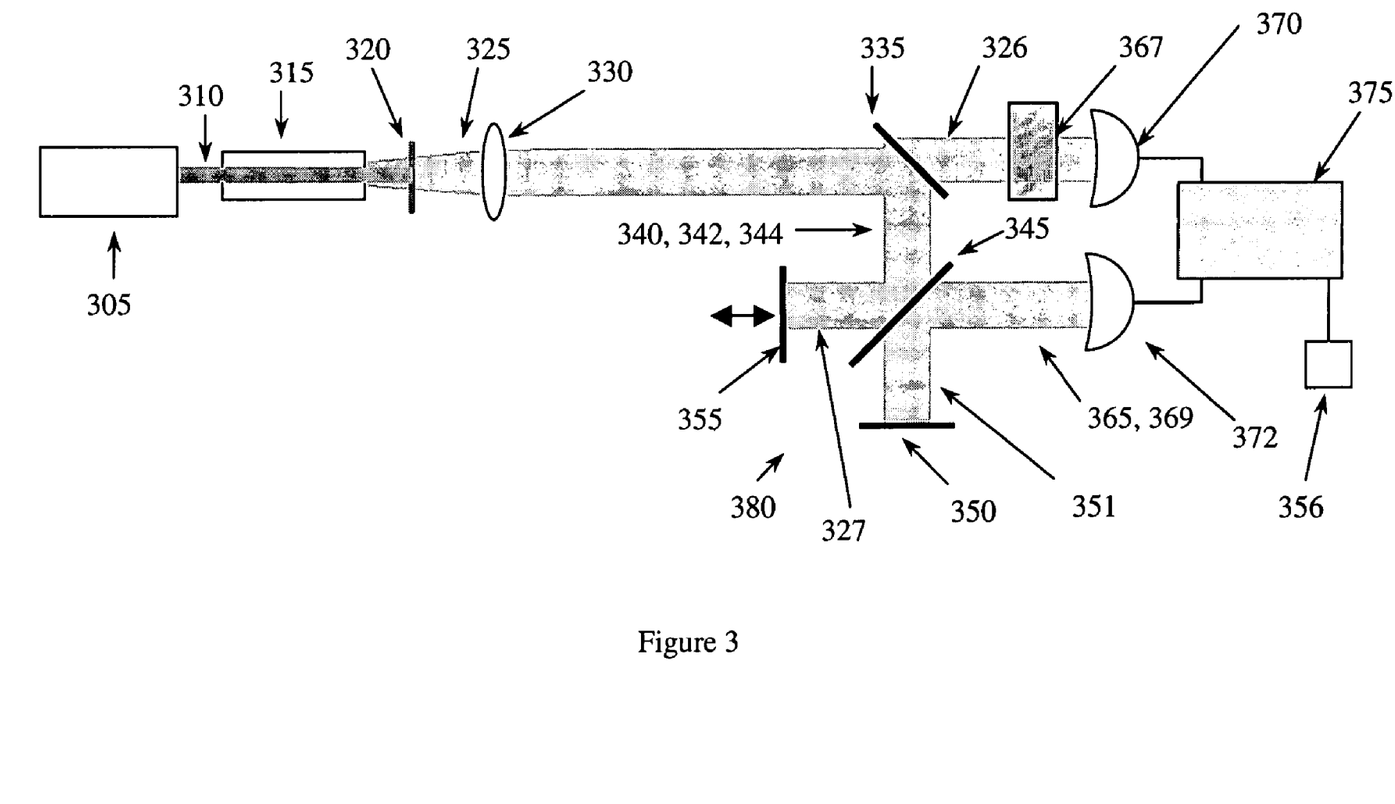
FIG. 3 is a schematic diagram of an entangled-photon Fourier transform spectrometer embodiment using a Michelson interferometer.

FIG. 3 is a schematic diagram of an entangled-photon spectrometer embodiment using a Michelson interferometer 380. This embodiment is enhanced with an improved signal-to-noise ratio compared to conventional spectrometers employing Michelson interferometers by use of entangled photons as describe herein. Laser 305 produces pump photons 310, which are directed into nonlinear crystal 315 with a high second order susceptibility. Filter 320 blocks any pump beam photons that might have passed through nonlinear crystal 315, while allowing the downconverted entangled-photon pairs to pass. A collimating lens 330 collimates the beam of entangled photons, which is split into signal photons 326 and idler photons 340 by polarizing beam splitter 335. Signal photons 326 are directed to sample 367, and those signal photons that are not absorbed are detected by detector 370. (The embodiment of FIG. 3 may be adapted to accommodate any, or a combination, of absorption, reflection, transmission, and scattering spectroscopy.) Idler photons 340 are directed to Michelson interferometer 380, and then directed to photon counting detector 372. The detection events from the photon counting detectors are analyzed by a coincidence counter 375. Conventional computer hardware or software 356 further processes data from coincidence counter 375 according to the following analysis.

Michelson interferometer 380 employs a beam splitter 345 for creating first transmitted beam 351 and first reflected beam 327 from incident idler photon beam 340. Fixed mirror 350 reflects first transmitted beam 351 back toward beam splitter 345, which splits first transmitted beam 351 into second transmitted beam 342 and second reflected beam 365. Movable mirror 355 reflects first reflected beam 327 back to beam splitter 345, which splits first reflected beam 327 into third transmitted beam 369 and third reflected beam 344 such that third transmitted beam 369 constructively or destructively interferes with second reflected beam 365 depending on the idler photon frequency and the position of movable mirror 355.

The probability of detecting an idler photon at detector 372 is modulated by the position of movable mirror 355 according to, by way of non-limiting example:

$$P_i(\tau, \omega_i) = \frac{1 + \cos(\omega_i \tau)}{2} \eta_i(\omega_i). \quad (10)$$

In equation (10), $\eta_i$ is the quantum efficiency of the idler photon detector 372 at the frequency $\omega_i$ of the idler photon, and $\tau$ is the relative time delay between interferometer paths induced by movable mirror 355. The probability of detecting a signal photon at detector 370 is proportional to the transmittance (or reflectance) of the sample, as represented by way of non-limiting example as:

$$P_s(\omega_s) = T(\omega_s)\eta_s(\omega_s). \quad (11)$$

In equation (11), T is the transmittance and $\eta_s$ is the quantum efficiency of the signal photon detector at the signal photon frequency $\omega_s$. The coincidence count rate may be written as, by way of non-limiting example:

$$\Phi_{cc}(\tau) = \Phi_{bi} \int_0^\infty \int_0^\infty \Psi(\omega_s, \omega_i) P_s(\omega_s) P_i(\tau, \omega_i) d\omega_i d\omega_s. \quad (12)$$

In equation (12), $\Phi_{bi}$ is the flux of biphotons and $\Psi$ is the two-dimensional spectral density of the biphoton source (which accounts for the bandwidth of the pump beam). This rate does not include accidental coincidences, which may result from the coincident detection of a signal photon with an idler photon other than its twin, a background photon, or a dark count. The total accidental coincident rate, including background and dark counts, may be written as, by way of non-limiting example:

$$\Phi_{bg}(\tau) = \left[\Phi_{bi}\int_0^\infty \left(\int_0^\infty \Psi(\omega_s,\omega_i)d\omega_i\right)P(\omega_s)d\omega_s + \Phi_{s\_bg}\right]\left[\Phi_{bi}\int_0^\infty \left(\int_0^\infty \Psi(\omega_s,\omega_i)d\omega_s\right)P(\tau,\omega_i)d\omega_i + \Phi_{i\_bg}\right]T_c. \quad (13)$$

In equation (13), $\Phi_{s\_bg}$ and $\Phi_{i\_bg}$ are the background plus dark count rates at the signal photon detector 370 and idler photon detector 372, respectively, and $T_c$ is the coincidence interval. The terms inside the brackets are the total individual count rates at the two detectors.

Assume for purposes of illustration that the biphoton spectral density can be represented as:

$$\Psi(\omega_s,\omega_i) = \delta(\omega_p - \omega_s - \omega_i)\Omega\mathrm{rect}\left(\frac{\omega_s - \omega_{s0}}{\Omega}\right)\mathrm{rect}\left(\frac{\omega_i - \omega_{i0}}{\Omega}\right). \quad (14)$$

Equation (14) describes an infinitely narrow pump beam and rectangular signal and idler spectra for purposes of illustration. The coincidence count rate and background count rates may respectively be represented as, by way of non-limiting example:

$$\Phi_{cc}(\tau) = \frac{\Phi_{bi}}{2\Omega}\int_{\omega_{i0}-\frac{\Omega}{2}}^{\omega_{i0}+\frac{\Omega}{2}} \eta_i(\omega_i)\eta_s(\omega_p - \omega_i)T(\omega_p - \omega_i)(1 + \cos(\omega_i\tau))d\omega_i, \quad (15)$$

$$\Phi_{bg}(\tau) = \left[\frac{\Phi_{bi}}{\Omega}\int_{\omega_{i0}-\frac{\Omega}{2}}^{\omega_{i0}+\frac{\Omega}{2}} \eta_s(\omega_s)T(\omega_s)d\omega_s + \Phi_{s\_bg}\right]\left[\frac{\Phi_{bi}}{2\Omega}\int_{\omega_{i0}-\frac{\Omega}{2}}^{\omega_{i0}+\frac{\Omega}{2}} \eta_i(\omega_i)(1 + \cos(\omega_i\tau))d\omega_i + \Phi_{i\_bg}\right]T_c. \quad (16)$$

In the case where the quantum efficiencies are not frequency dependent, equation (15) reduces to, by way of non-limiting example:

$$\Phi_{cc}(\tau) = \frac{\Phi_{cc}(0)}{2} + \frac{\Phi_{bi}}{2}\eta_i\eta_s\mathcal{J}_c\left(T(\omega_p - \omega)\mathrm{rect}\left(\frac{\omega - \omega_{i0}}{\Omega}\right)\right). \quad (17)$$

In equation (17), $\mathcal{J}_c$ is the Fourier cosine transform. The coincidence count rate when movable mirror 255 is set such that the optical path length of the two arms of the Michelson interferometer are equal ($\tau$=0) may be represented as, by way of non-limiting example:

$$\Phi_{cc}(0) = \frac{\Phi_{bi}\eta_i\eta_s}{\Omega}\int_{\omega_{i0}-\frac{\Omega}{2}}^{\omega_{i0}+\frac{\Omega}{2}} T(\omega)d\omega = \Phi_{bi}\eta_i\eta_s\overline{T}. \quad (18)$$

In equation (18), $\overline{T}$ is the average transmittance over the signal bandwidth. Where the quantum efficiencies are not frequency dependent, the background count rate reduces to, by way of non-limiting example:

$$\Phi_{bg}(\tau) = [\Phi_{bi}\eta_s\overline{T} + \Phi_{s\_bg}]\left[\frac{\Phi_{bi}\eta_i}{2}(1 + \mathrm{sinc}(\Omega\tau)) + \Phi_{i\_bg}\right]T_c. \quad (19)$$

For comparisons to conventional Fourier transform techniques, the following considers the case where the sample is in the idler photon path. Under the conditions described above in reference to equation (18), the coincidence count rate and background count rate respectively may accordingly be written as, by way of non-limiting example:

$$\Phi_{cc}(\tau) = \frac{\Phi_{bi}\eta_i\eta_s}{2}\left(\overline{T} + \mathcal{J}_c\left(T(\omega)\mathrm{rect}\left(\frac{\omega - \omega_{i0}}{\Omega}\right)\right)\right), \quad (20)$$

$$\Phi_{bg}(\tau) = [\Phi_{bi}\eta_s + \Phi_{s\_bg}]\left[\frac{\Phi_{bi}\eta_i}{2}\left(\overline{T} + \mathcal{J}_c\left(T(\omega)\mathrm{rect}\left(\frac{\omega - \omega_{i0}}{\Omega}\right)\right)\right) + \Phi_{i\_bg}\right]T_c. \quad (21)$$

In equations (20) and (21), $\overline{T}$ is the average transmittance over the idler bandwidth.

In equation (21), that the first term in the second bracket differs from the coincident count rate by a factor of $\eta_s$. The signal-to-noise ratio for a corresponding conventional (non-entangled-photon) Fourier transform spectrometer is estimated presently for the purposes of comparison with the embodiment of FIG. 3. The signal-to-noise ratio for such a conventional spectrometer may be written as, by way of non-limiting example:

$$SNR_{trad}(\tau) = \frac{\sqrt{\frac{\Phi_{bi}\eta_i}{2}\left(\overline{T} + \mathcal{J}_c\left(T(\omega)\mathrm{rect}\left(\frac{\omega - \omega_{i0}}{\Omega}\right)\right)\right)}}{\sqrt{2B\left[1 + \frac{\Phi_{i\_bg}}{\frac{\Phi_{bi}\eta_i}{2}\left(\overline{T} + \mathcal{J}_c\left(T(\omega)\mathrm{rect}\left(\frac{\omega - \omega_{i0}}{\Omega}\right)\right)\right)}\right]}}. \quad (22)$$

By contrast, the entangled-photon Fourier transform spectrometer embodiment of FIG. 3 (where the background count rate is estimated from the individual count rates) has a signal-to-noise ratio that may be represented as, by way of non-limiting example:

$$SNR_{ent}(\tau) = \frac{\left(\sqrt{\frac{\Phi_{bi}\eta_i\eta_s}{2}(\overline{T} + \mathcal{J}_c(T(\omega)\text{rect}(\frac{\omega-\omega_{i0}}{\Omega})))}\right)}{\left(\sqrt{2B\left[1 + \frac{[\Phi_{bi}\eta_s + \Phi_{s\_bg}]\frac{\Phi_{bi}\eta_i}{2}(\overline{T} + \mathcal{J}_c(\overline{T}(\omega)\text{rect}(\frac{\omega-\omega_{i0}}{\Omega}))) + \Phi_{i\_bg}]T_c}{\frac{\Phi_{bi}\eta_i\eta_s}{2}(\overline{T} + \mathcal{J}_c(T(\omega)\text{rect}(\frac{\omega-\omega_{i0}}{\Omega})))}\right]}\right)}. \quad (23)$$

At $\tau=0$, the signal-to-noise ratio of the conventional Fourier transform spectrometer described in reference to equation (22) may be written as, by way of non-limiting example:

$$SNR_{trad}(0) = \frac{\sqrt{\Phi_{bi}\eta_i\overline{T}}}{\sqrt{2B\left[1 + \frac{\Phi_{i\_bg}}{\Phi_{bi}\eta_i\overline{T}}\right]}}. \quad (24)$$

In contrast, the signal-to-noise ratio when $\tau=0$ of the entangled-photon Fourier transform spectrometer embodiment of FIG. 3, but with the sample in the idler photon arm described above in reference to equation (23), may be written as, by way of non-limiting example:

$$SNR_{ent}(0) = \frac{\sqrt{\Phi_{bi}\eta_i\eta_s\overline{T}}}{\sqrt{2B\left[1 + \frac{[\Phi_{bi}\eta_s + \Phi_{s\_bg}][\Phi_{bi}\eta_i\overline{T} + \Phi_{i\_bg}]T_c}{\Phi_{bi}\eta_i\eta_s\overline{T}}\right]}}. \quad (25)$$

Thus, for $\tau=0$, the ratio of the entangled-photon Fourier transform spectrometer signal-to-noise ratio to the conventional Fourier transform spectrometer signal-to-noise ratio may be written as, by way of non-limiting example:

$$\frac{SNR_{ent}(0)}{SNR_{trad}(0)} = \frac{\eta_s\sqrt{\Phi_{bi}\eta_i\overline{T} + \Phi_{i\_bg}}}{\sqrt{\Phi_{bi}\eta_i\eta_s\overline{T} + [\Phi_{bi}\eta_s + \Phi_{s\_bg}][\Phi_{bi}\eta_i\overline{T} + \Phi_{i\_bg}]T_c}} \quad (26)$$

$$= \frac{\sqrt{\eta_s}\sqrt{1 + \frac{\Phi_{i\_bg}}{\Phi_{bi}\eta_i\overline{T}}}}{\sqrt{\left[1 + \Phi_{bi} + \frac{\Phi_{i\_bg}}{\eta_i\overline{T}} + \frac{\Phi_{s\_bg}}{\eta_s} + \frac{\Phi_{s\_bg}\Phi_{i\_bg}}{\Phi_{bi}\eta_i\eta_s\overline{T}}\right]T_c}}.$$

In the background-limited case, equation (26) may be approximated as, by way of non-limiting example:

$$\frac{SNR_{ent}(0)}{SNR_{trad}(0)} \approx \frac{\eta_s}{\sqrt{\Phi_{s\_bg}T_c}}. \quad (27)$$

Accordingly, in the background-limited case, the entangled-photon Fourier transform spectrometer is superior to conventional Fourier transform spectrometers whenever the product of the coincidence interval with the background and dark count rates at signal photon detector 370 is less than the square of the signal photon detector quantum efficiency. This condition may be represented as, by way of non-limiting example:

$$\Phi_{s\_bg}T_c < \eta_s^2. \quad (28)$$

In the signal-limited case, equation (26) may be approximated as, by way of non-limiting example:

$$\frac{SNR_{ent}(0)}{SNR_{trad}(0)} = \frac{\sqrt{\eta_s}}{\sqrt{\Phi_{bi}T_c}}. \quad (29)$$

Accordingly, in the signal-limited case, the entangled-photon Fourier transform spectrometer is superior to conventional Fourier transform spectrometers whenever the product of the coincidence interval with the biphoton flux is less than the signal photon detector quantum efficiency. This condition may be represented as, by way of non-limiting example:

$$\Phi_{bi}T_c < \eta_s. \quad (30)$$

Figure 4:
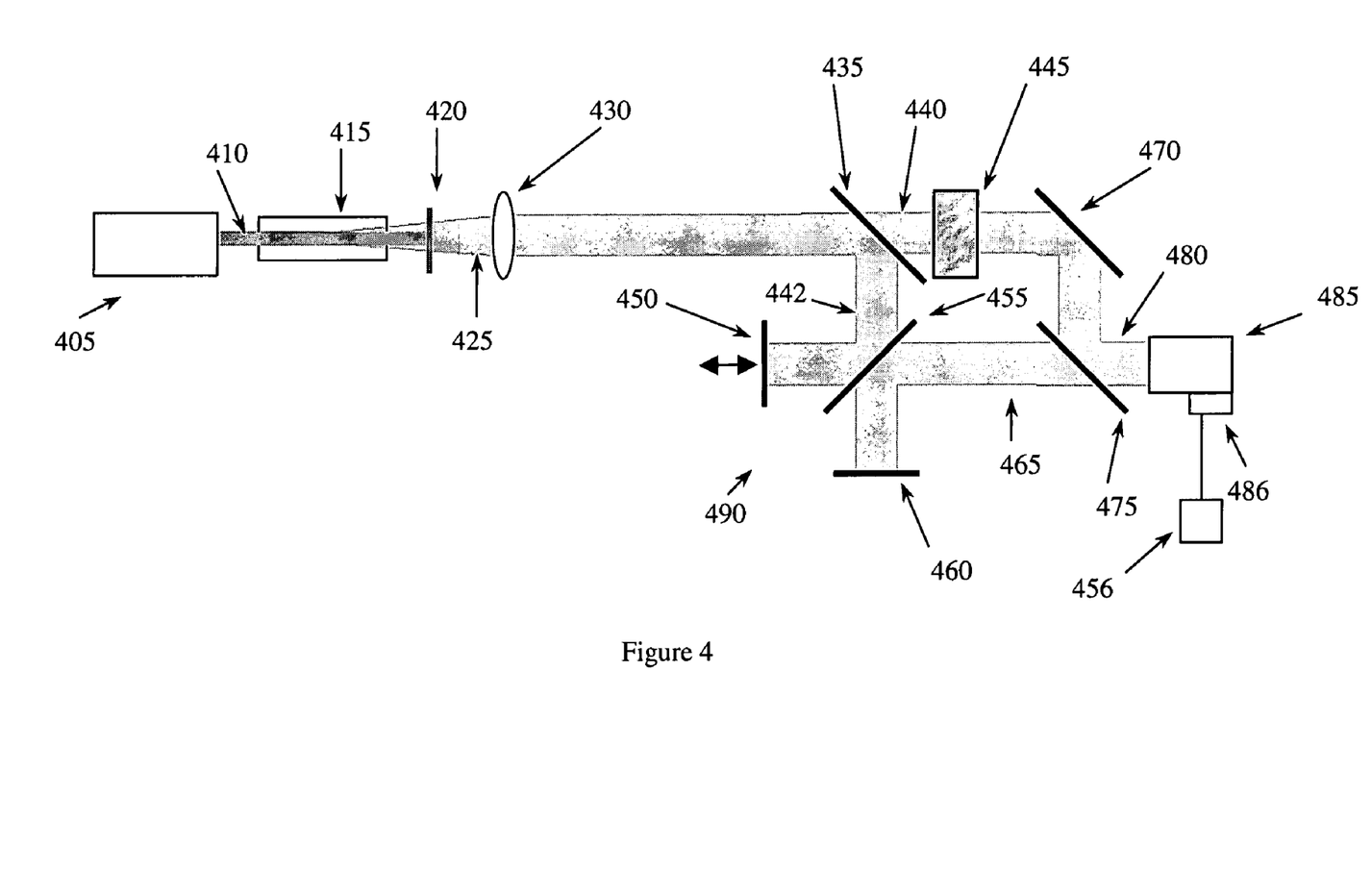
FIG. 4 is schematic diagram of a biphoton sensitive material entangled-photon spectrometer embodiment.

The conditions discussed above in reference to equations (28) and (30) imply that the entangled-photon Fourier transform spectrometer of FIG. 3 is superior to conventional Fourier transform spectrometers whenever the probability that a photon is detected in a coincidence interval is relatively small (e.g., for relatively weak biphoton sources). For a bright biphoton source, this may be accomplished by using a biphoton sensitive material, where the effective coincidence interval duration is on the order of the entanglement time, which is on the order of picoseconds. FIG. 4 describes such an embodiment.

FIG. 4 is schematic diagram of an entangled-photon Fourier transform spectrometer embodiment employing a biphoton sensitive material ("BSM"). Detailed descriptions of various BSM are found in U.S. patent application Ser. No. 10/850,394, to Kastella et al., filed on May 21, 2004. The BSM may be, by way of non-limiting example, rubidium-87. Such a BSM is substantially opaque to entangled-photon pairs, while being substantially transparent to random photon pairs. When a BSM absorbs an entangled-photon pair, it produces an indicia of absorption, such as a fluorophoton, which may be detected. Laser 405 produces pump photons 410, which are directed to nonlinear crystal 415. Nonlinear crystal produces signal photons and idler photons from pump photons 410. Filter 420 blocks any pump beam photons that might have passed through nonlinear crystal 415, while allowing the entangled-photon pairs to pass. A collimating lens 430 collimates the beam of entangled photons, which is split into signal photon beam 440 and idler photon beam 442 by a beam splitter 435. Signal photons 440 are directed to sample 445 and those that are not absorbed are reflected off mirror 470, which directs the transmitted photons to beam splitter 475 into the path of idler photon beam 465 exiting Michelson interferometer 490. Idler photons are directed to Michelson interferometer, which is configured as Michelson interferometer 480 of FIG. 4 above. Idler photons exiting Michelson interferometer 490 are directed through beam splitter 475, which remixes the idler photons with signal photons into combined photon beam 480. Combined photon beam 480 is directed to BSM 485. BSM 485 is operatively coupled with biphoton-absorption detector 486, which detects indicia of biphoton absorption such as fluorophoton emission. Biphoton-absorption detector 486 is coupled to electronic processing equipment 456, which processes the detection events in accordance with equation (31) below. For the embodiment of FIG. 4, the analytical expression for the biphoton coincidence count rate $\Phi_{cc}$ is given as, by way of non-limiting example:

$$\Phi_{cc}(\tau) = \frac{\Phi_{bi}}{2} \int_0^\infty \int_0^\infty \Psi(\omega_s, \omega_i) T(\omega_s)(1 + \cos(\omega_i \tau)) \eta(\omega_s, \omega_i) d\omega_i d\omega_s. \quad (31)$$

The embodiment of FIG. 4 is not limited by the speed of conventional electronic coincidence counters, which place limitations on the maximum photon flux. Embodiments of entangled-photon spectrometers that use a BSM may employ high fluxes, which correspondingly decrease the time necessary to collect data for computing the spectrum.

Figure 5:
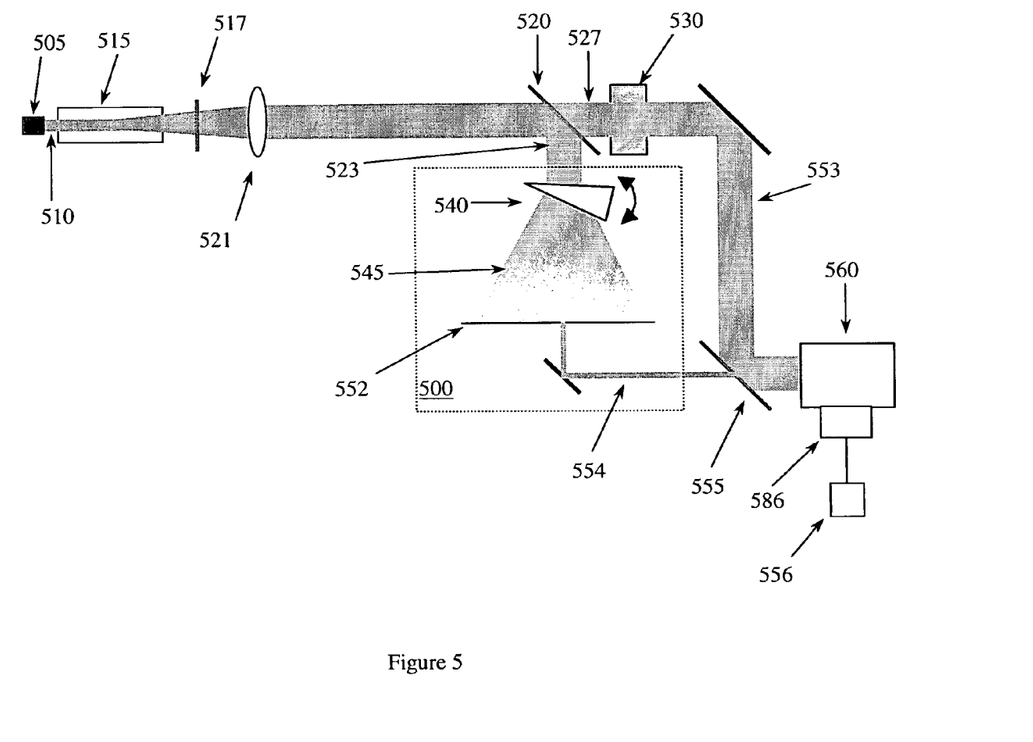
FIG. 5 is a schematic diagram of an entangled-photon spectrometer embodiment employing a monochromator and employing a biphoton sensitive material.

FIG. 5 is a schematic diagram of a BSM entangled-photon spectrometer embodiment employing a monochromator. As in the embodiment of FIG. 2, laser 505 produces pump beam 510, which is directed to nonlinear crystal 515. Filter 517 blocks remaining pump beam photons that may have passed through nonlinear crystal 515. Collimating lens 521 collimates the entangled photon pairs, which are then separated into signal photons 527 and idler photons 523 by polarizing beam splitter 520. Next, signal photons 527 are directed at sample 530. Signal photons 533 that are not absorbed are detected by signal photon detector 535. Idler photons 523 are directed to monochromator configuration 500 in order to select idler photons of a particular frequency. Monochromator configuration 500 includes pivotable dispersive element 540 (e.g., a prism or a grating), which separates idler photons 545 according to frequency. Aperture 552 is interposed after dispersive element 540 in order to pass only idler photons 554 of the frequency of interest from monochromator 500. Signal photons 553 from sample 530 together with selected idler photons 554 are together directed to BSM 560. Additional optical delay lengths may be interposed into signal photon 553 path or idler photon 554 path as required to ensure that the constituent photons of each entangled-photon pair arrive at BSM 560 within the entanglement time. Detector 586 detects indicia of entangled-photon absorption by BSM 560. As in the embodiment of FIG. 2, detection events are sent to computer 556, which processes the information as described above in reference to equations (1)-(9) and the embodiment of FIGS. 3 and 4 in order to produce spectrometric information regarding sample 530.

In another BSM entangled-photon spectroscopy embodiment, the signal photon and idler photon beams are directed into opposite ends of a BSM. Measurements at different frequencies are made by arranging the dispersive system such that each frequency has a different path length. The biphoton detector only responds to pairs of photons that have traveled equal optical paths lengths, so different frequencies (corresponding to path delays) map to different locations within the BSM. Embodiments using a BSM are relatively immune to background radiation and can be used to measure the index of refraction of the sample.

Figure 6:
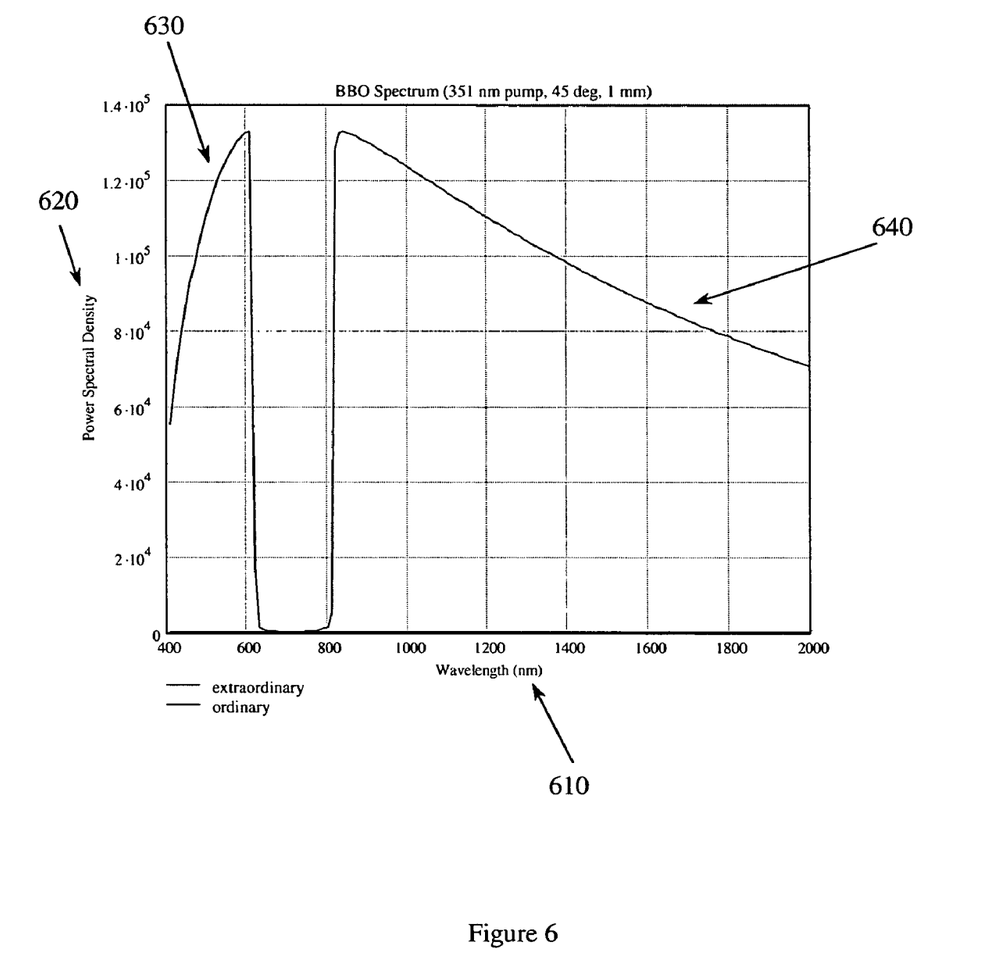
FIG. 6 is a graph depicting a power spectrum for non-degenerate biphotons.

FIG. 6 is a graph depicting a power spectrum for non-degenerate biphotons. The x-axis represents the photon wavelengths, and the y-axis represents the power spectral density. Curve 630 represents higher-energy idler photons, which are entangled with lower-energy signal photons represented by curve 640. Because non-degenerate entangled photons may be produced as illustrated by the graph of FIG. 6, entangled-photon spectrometer embodiments according to the present invention may be configured to direct photons of one frequency at a sample of interest, while using photons of a different frequency as disclosed herein in order to affect an improved signal-to-noise ratio.

Any type of interferometer may be used in embodiments of the present invention that employ an interferometer. Types of interferometers that may be used include, by way of non-limiting example, Michelson and Mach-Zender. Modifications of these and other interferometers may also be used.

In embodiments of the present invention, the signal photon detector can be made to encompass the sample, such that all scattered photons are detected as well.

In embodiments of the present invention, any number of signal photon detectors may be used to measure transmittance, scattering, or reflectance independently and simultaneously. Whereas conventional spectrometers only determine the fraction of light transmitted and cannot distinguish between losses due to absorption or due to scattering, embodiments of the present invention can measure both.

Embodiments of the present invention typically use a "computer" to calculate spectroscopic information from observed data. Such a computer may be a stand-alone device or internal to the spectroscopic apparatus and/or coincidence counter. The computer may comprise an application-specific integrated circuit (ASIC), a programmed computer, or software running on a general purpose machine. In embodiments of the present invention, the term "computer" is not meant to be restrictive; rather, it is meant to encompass any hardware or software capable of performing the calculations detailed herein.

In embodiments of the present invention, the idler photon detector array need not be located in proximity to the signal photon detector. All that is necessary is that the pulses from detection events on all receivers be relayed to the coincidence counter (in real-time or via playback from a recording) and that the optical path difference between signal photon and idler photon detectors be known to within a time small compared to the coincidence window duration.

Note that in any of the embodiments described herein, either the signal photons or the idler photons may be directed to the sample. More generally, the terms "signal" and "idler" may be used interchangeably.

Entangled photons may be produced according to a variety of methods. By way of non-limiting example, entangled photons may be produced according to types I or II parametric down-conversion. That is, biphotons whose constituent signal and idler photons are orthogonally polarized may be used as well as biphotons whose constituent signal and idler photons are polarized in parallel. For type-I downconversion, signal photons may be separated from idler photons (and recombined with idler photons) using dichroic glass/mirrors. For both types of downconversion, signal photons and idler photos may be selected as they exit the biphoton source by providing apertures at the appropriate angles. Furthermore, any nonlinear crystal, not limited to BBO, may be used. Other ways to produce entangled photons include: excited gasses, materials without inversion symmetry, and generally any properly phase-matched medium. Entangled photon production consistent with this disclosure is not limited to using BBO or any other particular non-linear crystal. Furthermore, the entangled photons are not limited to any particular wavelength or frequency. Biphotons whose constituent signal and idler photons are orthogonally polarized may be used as well as biphotons whose constituent signal and idler photons are polarized in parallel.

In other embodiments of the present invention that employ a BSM, various indicia of entangled-photon absorption by the BSM may be used to detect entangled photons. By way of non-limiting example, entangled-photon absorption may result in fluorescence, phosphorescence, direct electron transfer, or ionization of the absorbing material. Detecting fluorescence, phosphorescence, direct electron transfer, or ionization may be used to detect entangled-photon absorption. Also by way of non-limiting example, avalanche photodiodes, photo multiplier tubes, or other devices may be used to detect the fluorophotons, ionization, direct electron transfer, or other absorption indicia.

In other embodiments of the invention, the BSM is not limited to $^{87}$Rb. By way of non-limiting example, any material with appropriately structured energy levels, such as cesium-133 ($^{133}$Cs) or other alkalis may be used. Preferably, such materials are those with a very narrow multi-photon absorption linewidth. More preferably, such materials are those with a very narrow multi-photon transition to an excited state that decays through a path that includes a radiative transition. Appropriate BSM materials may be in solid, liquid, gaseous, or plasma states. Colloids are also contemplated. In some embodiments of the present invention, quantum dots may be used. Further, embodiments of the invention are not limited to any particular ETPA or RTPA electron energy level transition. Pump, signal, and idler photon frequencies and wavelengths may vary from those disclosed herein.

The embodiments disclosed herein have wide applications in industry and research for performing spectroscopic measurements of chemical species and bio-agents in the far IR and THz regions where conventional spectrometers have limited detection. Additionally, these embodiments afford the possibility of performing broadband spectroscopy at a distance. For example, spectroscopy may be conducted on atmospheric contaminants over significant distances using a low-level light source that poses no environmental hazards. In the area of medical applications, the disclosed embodiments can perform routine analysis of blood and urine samples or perform non-invasive spectroscopy of in vivo samples without necessitating cumbersome optical setups as required by conventional spectrometry, because all that is required in the signal photon arm is a photon counting detector connected electronically to a coincidence counter.

The equations contained in this disclosure are illustrative and representative and are not meant to be limiting. Alternate equations may be used to represent the same phenomena described by any given equation disclosed herein. For example, the equations disclosed herein may be modified by adding error-correction terms, higher-order terms, or otherwise accounting for inaccuracies, using different names for constants or variables, or using different expressions. Other modifications, substitutions, replacements, or alterations of the equations may be performed.

The particular optical manipulation devices depicted herein are illustrative and representative and are not meant to be limiting. By way of non-limiting example, the prisms, and lenses disclosed herein may be replaced with devices known to those of ordinary skill in the art.

Other embodiments and uses of the invention will be apparent to those skilled in the art from consideration of the specification and applications of the invention disclosed herein. The specification and details of the analytical expressions should be considered exemplary only. The foregoing examples have been provided merely for the purpose of explanation and are in no way to be construed as limiting of the present invention. While the present invention has been described with reference to certain embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method of determining spectroscopic information of a portion of matter, the method comprising:
producing a first photon beam and a second photon beam, each photon in at least a portion of the first photon beam being entangled with at least one photon in the second photon beam;
causing photons from the first photon beam to interact with the portion of matter to produce first photons;
processing the second beam to produce second photons;
detecting at least one coincidence, each coincidence occurring between a first photon and a second photon, to derive a coincidence parameter;
calculating from the coincidence parameter, using a computer, spectroscopic information relating to the portion of matter; and
outputting the spectroscopic information.

2. The method of claim 1 wherein the first photons comprise photons selected from the group consisting of photons transmitted by the portion of matter, photons reflected by the portion of matter, and photons scattered by the portion of matter.

3. The method of claim 1 wherein said processing comprises processing with an interferometer.

4. The method of claim 3 wherein the interferometer comprises an interferometer selected from the group consisting of Michelson interferometer and Mach-Zender interferometer.

5. The method of claim 1 wherein said processing comprises selecting a frequency.

6. The method of claim 1 wherein said processing comprises separating by frequency.

7. The method of claim 1 wherein said detecting comprises using an electronic coincidence counter.

8. The method of claim 1 wherein said detecting comprises using an entangled photon sensitive material.

9. The method of claim 1 wherein the coincidence parameter comprises a number of coincidences in a time interval.

10. The method of claim 1 wherein the coincidence parameter comprises a ratio of coincidence detection counts.

11. The method of claim 1 wherein the first photon beam includes far infrared photons.

12. The method of claim 1 wherein the first photon beam comprises terahertz photons.

13. The method of claim 1 wherein the portion of matter is remote from a location of said detecting.

14. The method of claim 1 further comprising calibrating, wherein said calibrating comprises determining a quantum efficiency of a detector, the detector being configured to detect at least a portion of the first photons.

15. A system for determining spectroscopic information of a portion of matter, the system comprising:
- means for producing a first photon beam and a second photon beam, each photon in at least a portion of the first photon beam being entangled with at least one photon in the second photon beam;
- means for directing the first beam to interact with the portion of matter to produce interacted photons;
- means for processing the second beam to produce processed photons;
- means for detecting at least one coincidence, each coincidence occurring between an interacted photon and a processed photon, to derive a coincidence parameter; and
- a computer configured to use the coincidence parameter to derive spectroscopic information relating to the portion of matter.

16. The system of claim 15 wherein said means for detecting comprises a means for detecting at least one coincidence, each coincidence occurring between a processed photon and a photon selected from the group consisting of photons transmitted by the portion of matter, photons reflected by the portion of matter, and photons scattered by the portion of matter.

17. The system of claim 15 wherein said means for processing comprises an interferometer.

18. The system of claim 17 wherein the interferometer comprises an interferometer selected from the group consisting of Michelson interferometer and Mach-Zender interferometer.

19. The system of claim 15 wherein said means for processing comprises a monochromator.

20. The system of claim 15 wherein said means for processing comprises a dispersive element.

21. The system of claim 15 wherein said means for detecting comprises an electronic coincidence counter.

22. The system of claim 15 wherein said means for detecting comprises an entangled photon sensitive material.

23. The system of claim 15 wherein the coincidence parameter comprises a number of coincidences in a time interval.

24. The system of claim 15 wherein the coincidence parameter comprises a ratio of coincidence detection counts.

25. The system of claim 15, wherein the first photon beam includes far infrared photons.

26. The system of claim 15, wherein the first photon beam comprises terahertz photons.

27. The system of claim 15, wherein the portion of matter is remote from said means for detecting.

28. The system of claim 15 configured to be calibrated by determining a quantum efficiency of a detector, the detector being configured to detect at least a portion of the photons that have interacted with the portion of matter.

29. A system for determining spectroscopic information of a portion of matter, the system comprising:
- a source of entangled photons;
- optics configured to receive a first portion of photons, the first portion of photons having interacted with the portion of matter, the first portion of photons comprising a portion of the entangled photons;
- a dispersive element configured to receive a second portion of photons and output a third portion of photons, each photon in the second portion of photons being entangled with at least one photon in the first portion of photons;
- a coincidence counter configured to detect at least one coincidence, each coincidence occurring between a photon in the first portion of photons and a photon in the third portion of photons, to derive a coincidence parameter; and
- a computer configured to use the coincidence parameter to derive spectroscopic information relating to the portion of matter.

30. The system of claim 29 wherein said first portion of photons comprise photons selected from the group consisting of photons transmitted by the portion of matter, photons reflected by the portion of matter, and photons scattered by the portion of matter.

31. The system of claim 29 further comprising a monochromator comprising said dispersive element.

32. The system of claim 29 wherein said coincidence counter comprises an electronic coincidence counter.

33. The system of claim 29 wherein said coincidence counter comprises an entangled photon sensitive material.

34. The system of claim 29 wherein the coincidence parameter comprises a number of coincidences in a time interval.

35. The system of claim 29 wherein the coincidence parameter comprises a ratio of coincidence detection counts.

36. The system of claim 29, wherein the first portion of photons comprises far infrared photons.

37. The system of claim 29, wherein the first portion of photons comprises terahertz photons.

38. The system of claim 29, wherein the portion of matter is remote from said means for detecting.

39. The system of claim 29 configured to be calibrated by determining a quantum efficiency of a detector, the detector being configured to detect at least a portion of the first portion of photons.

40. A system for determining spectroscopic information of a portion of matter, the system comprising:
- a source of entangled photons;
- optics configured to receive a first portion of photons, the first portion of photons having interacted with the portion of matter, the first portion of photons comprising a portion of the entangled photons;
- an interferometer configured to receive a second portion of photons and output a third portion of photons, each photon in the second portion of photons being entangled with at least one photon in the first portion of photons;
- a coincidence counter configured to detect at least one coincidence, each coincidence occurring between a photon in the first portion of photons and a photon in the third portion of photons, to derive a coincidence parameter; and
- a computer configured to use the coincidence parameter to derive spectroscopic information relating to the portion of matter.

41. The system of claim 40 wherein said first portion of photons comprise photons selected from the group consisting of photons transmitted by the portion of matter, photons reflected by the portion of matter, and photons scattered by the portion of matter.

42. The system of claim 40 wherein the interferometer comprises an interferometer selected from the group consisting of Michelson interferometer and Mach-Zender interferometer.

43. The system of claim 40 wherein said coincidence counter comprises an electronic coincidence counter.

44. The system of claim 40 wherein said coincidence counter comprises an entangled photon sensitive material.

45. The system of claim 40 wherein the coincidence parameter comprises a number of coincidences in a time interval.

46. The system of claim 40 wherein the coincidence parameter comprises a ratio of coincidence detection counts.

47. The system of claim 40, wherein the first portion of photons comprises far infrared photons.

48. The system of claim 40, wherein the first portion of photons comprises terahertz photons.

49. The system of claim 40, wherein the portion of matter is remote from the coincidence counter.

50. The system of claim 40 configured to be calibrated by determining a quantum efficiency of a detector, the detector being configured to detect at least a portion of the first portion of photons.

51. A method of determining spectroscopic information of a portion of matter, the method comprising:
  producing a first photon beam and a second photon beam, each photon in at least a portion of the first photon beam being entangled with at least one photon in the second photon beam;
  directing photons from the first photon beam to interact with the portion of matter to produce first photons;
  causing a first portion of photons from the second photon beam to interfere with a second portion of photons from the second photon beam to produce second photons;
  detecting at least one coincidence, each coincidence occurring between a first photon and a second photon, to derive a coincidence parameter;
  calculating from the coincidence parameter, using a computer, spectroscopic information relating to the portion of matter; and
  outputting the spectroscopic information.

52. The method of claim 51 wherein the first photons comprise photons selected from the group consisting of photons transmitted by the portion of matter, photons reflected by the portion of matter, and photons scattered by the portion of matter.

53. The method of claim 51 wherein said detecting comprises using an electronic coincidence counter.

54. The method of claim 51 wherein said detecting comprises using an entangled photon sensitive material.

55. The method of claim 51 wherein the coincidence parameter comprises a number of coincidences in a time interval.

56. The method of claim 51 wherein the coincidence parameter comprises a ratio of coincidence detection counts.

57. The method of claim 51 wherein the first photon beam includes far infrared photons.

58. The method of claim 51 wherein the first photon beam comprises terahertz photons.

59. The method of claim 51 wherein the portion of matter is remote from a location of said detecting.

60. The method of claim 51 further comprising calibrating, wherein said calibrating comprises determining a quantum efficiency of a detector, the detector being configured to detect at least a portion of the first photons.

61. The method of claim 51 wherein said causing comprises using an interferometer selected from the group consisting of Michelson interferometer and Mach-Zender interferometer.

* * * * *